(12) United States Patent
Winter et al.

(10) Patent No.: US 7,908,925 B2
(45) Date of Patent: Mar. 22, 2011

(54) RESONANCE RESPONSE TESTING ON A BEARING

(75) Inventors: Robert Winter, Longmont, CO (US); Eddy Larson, Eric, CO (US); Shawn Salisbury, Niwot, CO (US)

(73) Assignee: Seagate Technology LLC, Scotts Valley, CA (US)

( * ) Notice: Subject to any disclaimer, the term of this patent is extended or adjusted under 35 U.S.C. 154(b) by 586 days.

(21) Appl. No.: 11/948,025

(22) Filed: Nov. 30, 2007

(65) Prior Publication Data

US 2009/0139302 A1 Jun. 4, 2009

(51) Int. Cl.
*G01N 29/12* (2006.01)
*G01N 3/56* (2006.01)
(52) U.S. Cl. ............... 73/660; 73/9; 73/11.01; 73/579
(58) Field of Classification Search .............. 73/660, 73/9, 11.01, 579; 360/265.6
See application file for complete search history.

(56) References Cited

U.S. PATENT DOCUMENTS

| | | | | |
|---|---|---|---|---|
| 2,359,044 | A | * | 9/1944 | MacBride ................... 73/844 |
| 3,498,518 | A | * | 3/1970 | Price et al. ................. 228/50 |
| 3,952,566 | A | * | 4/1976 | Jacobson ..................... 73/10 |
| 4,982,518 | A | * | 1/1991 | Guenther ................... 40/371 |
| 5,654,841 | A |   | 8/1997 | Hobson |
| 6,453,722 | B1 |   | 9/2002 | Liu |
| 6,563,661 | B2 | * | 5/2003 | Thia et al. ................ 360/75 |
| 6,606,224 | B2 |   | 8/2003 | Macpherson |
| 6,861,854 | B1 |   | 3/2005 | Guo |
| 7,054,111 | B2 | * | 5/2006 | Dominguez et al. ....... 360/265.6 |

* cited by examiner

*Primary Examiner* — Jacques M Saint Surin
(74) *Attorney, Agent, or Firm* — McCarthy Law Group

(57) ABSTRACT

An apparatus and associated method is provided for holding an inner race of a bearing stationary with respect to rotational movement while leaving a hub that is fixed in rotation with an outer race of the bearing unencumbered. The hub is excited by contactingly engaging it with a predetermined mechanical force. The resonance response of the hub to the excitation is determined and used to characterize the bearing qualitatively.

18 Claims, 5 Drawing Sheets

RESONANCE RESPONSE TESTING ON A BEARING

BACKGROUND

Machinery and methods employed in the manufacturing industry have been continuously shaped by a number of market and business forces. For example, many manufactured products today are relatively more complex than those in the past, as high technology electronics have proliferated and become integrated even into commonly used consumer goods. Flexibility is key to a manufacturer's survival, as smaller lot runs of products having different feature sets must be produced on the same production line. And while the functional capabilities and the number of offered features continually grows, miniaturization and portability are equally important market factors as well. Add to the mix the fact that price demands have forced a greater emphasis on manufacturing efficiency to the extent that processing station cycle time is often scrutinized to a fraction of a second.

To evolve in the face of these and other factors, manufacturers must continually strive to replace manual operations with highly-complex and processor-controlled automated systems. Factory reengineering efforts must be employed to perform inspections at the component level and to permit assembling components just-in-time, instead of batch processing the components as has been done in the past. To the extent possible, product design and process capability analyses must be directed toward building quality into the process, thereby reducing if not eliminating the amount of inspection activities.

Illustrative embodiments of the claimed invention are directed to the manufacture of an actuator assembly that operably supports a data transfer member adjacent a storage medium in a data storage device. The actuator assembly employs a cartridge bearing having a stationary shaft affixed to a base at one end and to a cover at the other end, the base and cover cooperatively forming an enclosure. An actuator body, sometimes referred to as an "e-block," is affixed to an external mount of the cartridge bearing and is thereby journaled in rotation with respect to the storage medium. The rotary motion of the actuator permits selectively locating the data transfer member adjacent any of a plurality of different data storage locations across the storage medium.

Static bearing characteristics, such as stiffness, are determined according to some previously attempted solutions by first assembling the actuator assembly together. That is, the body is assembled to the cartridge bearing and the body/bearing subassembly is assembled to the enclosure in order to test the bearing. The assembly time alone, which can easily take fifteen minutes to complete manually, is the critical path by far when such solutions are employed to sample bearings. The disassembly time is a harsh penalty to pay on finding a nonconformance when such solutions are employed in product assembly. What the related art solutions are lacking is a way to test static characteristics of the bearing at the component level.

SUMMARY

Claimed embodiments are generally directed to bearing testing for qualitatively characterizing a bearing.

In some embodiments an apparatus and associated method is provided for holding an inner race of a bearing stationary with respect to rotational movement while leaving a hub that is fixed in rotation with an outer race of the bearing unencumbered. The hub is excited by contactingly engaging it with a predetermined mechanical force. The resonance response of the hub to the excitation is determined and used to characterize the bearing qualitatively, such as but not limited to characterizing the bearing stiffness.

These and various other features and advantages which characterize the claimed embodiments will become apparent upon reading the following detailed description and upon reviewing the associated drawings.

DETAILED DESCRIPTION

Figure 1:
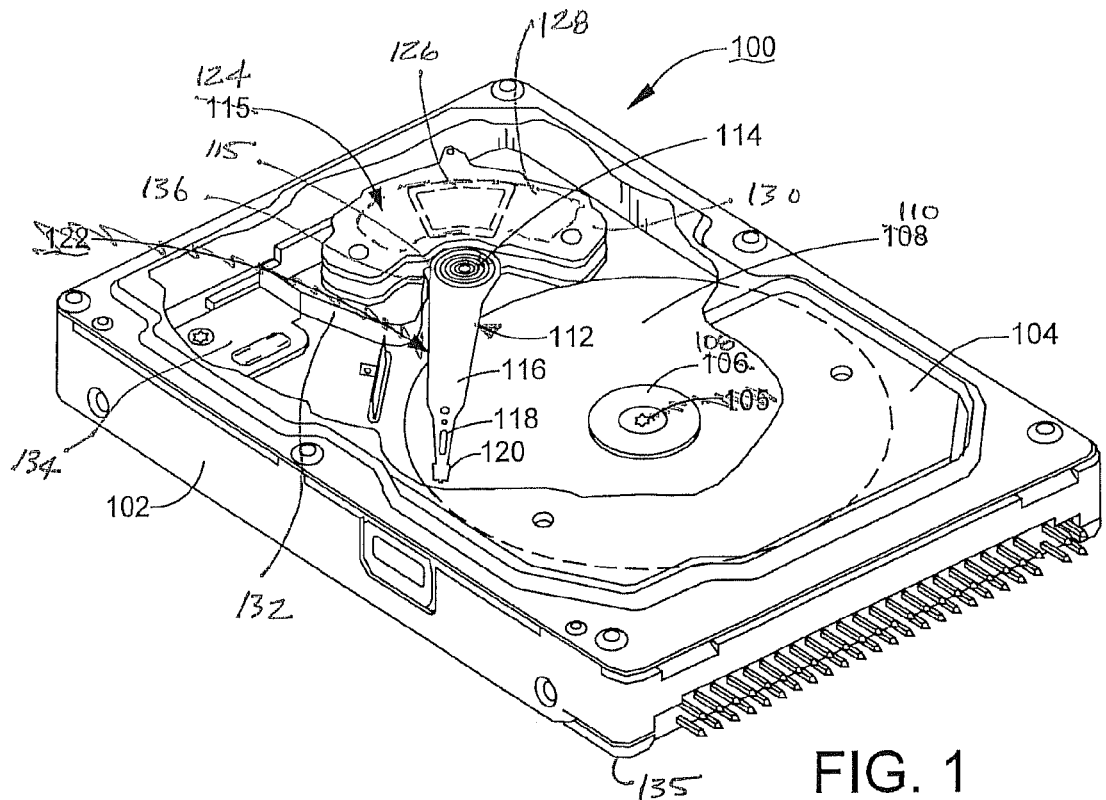
FIG. 1 is an isometric view of a data storage device that is constructed in accordance with embodiments of the present invention.

Referring to the drawings as a whole, and for now in particular to FIG. 1 which is an isometric view of a data storage device 100 that is constructed in accordance with embodiments of the present invention. A base 102 and a cover 104 (partially cutaway) with a sealing member interposed therebetween provide a sealed enclosure for a number of components. These components include a spindle motor 108 that has one or more data storage mediums (sometimes referred to as "discs") 110 affixed thereto in rotation.

Adjacent the disc 110 is an actuator assembly 112 that pivots by being supported by a cartridge bearing 114. The actuator assembly 112 includes an eblock 115 having a cantilevered actuator arm 116 supporting a load arm 118 that, in turn, supports a read/write transducer (or "head") 120 in a data transfer relationship with the adjacent disc 110.

A recording surface of the disc 110 is divided into a plurality of tracks over which the head 120 is moved. The tracks can have head position control information written to embedded servo sectors. Between the embedded servo sectors are data sectors for storing user data. The head 120 stores input data to the tracks and retrieves output data from the tracks. The output data can be previously stored user data or it can be servo data used to position-control the head 120 relative to a desired track.

The actuator assembly 112 is positionally controlled by a voice coil motor (VCM) 124 that includes an actuator coil 126 immersed in a magnetic field generated by a magnet assembly 128. A pair of steel plates 130 (pole pieces) mounted above and below the actuator coil 126 provides a magnetically permeable flux path for a magnetic circuit of the VCM 124. During operation of the data storage device 100 current is passed through the actuator coil 126 forming an electromagnetic field, which interacts with the magnetic circuit of the VCM 124, causing the actuator 112 to move the head 120 radially across the disc 110.

To provide the requisite electrical conduction paths between the head 120 and data storage device control circuitry, head wires of the head 120 are affixed to a flex circuit 132. The flex circuit 132 is routed at one end from the load arms 118 along the actuator arms 116, and is secured to a flex connector 134 at the other end. The flex connector 134 Supports the flex circuit 132 where it passes through the base 102 and into electrical communication with a printed circuit board assembly ("PCBA") 135, mounted to the underside of the base 102. A preamplifier/driver (preamp) 136 conditions read/write signals passed between the control circuitry and the head 120.

Figure 2:
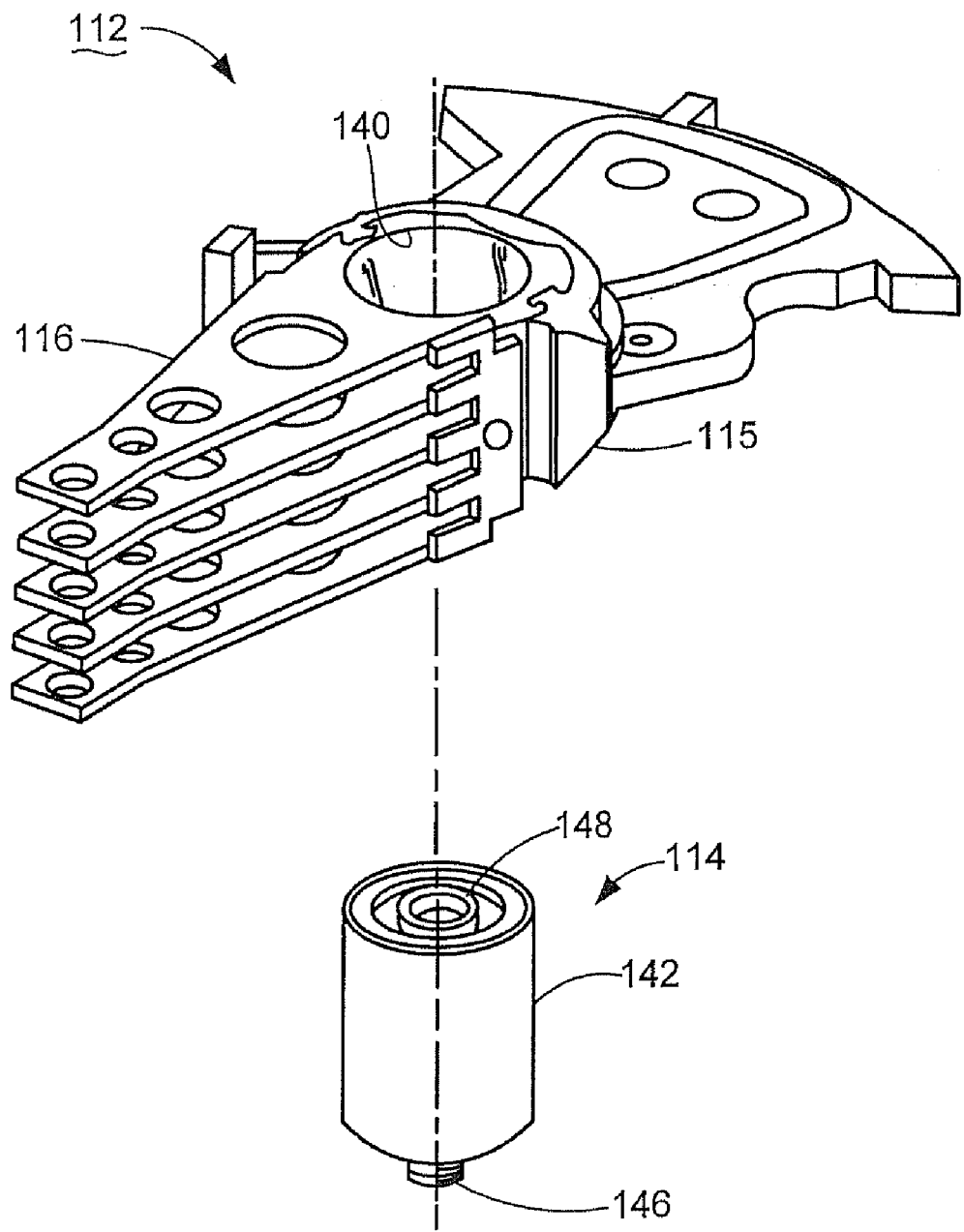
FIG. 2 is an exploded isometric view of the e-block and cartridge bearing in the actuator assembly of the data storage device of FIG. 1.

FIG. 2 is a partially exploded isometric view of the eblock 115 and cartridge bearing 114 portions of the actuator assembly 112. The eblock 115 defines a bore 140 that is sized to matingly engage an external mount 142 of the cartridge bearing 114 so that the eblock 115 and mount 142 are operably affixed together in rotation.

Figure 3:
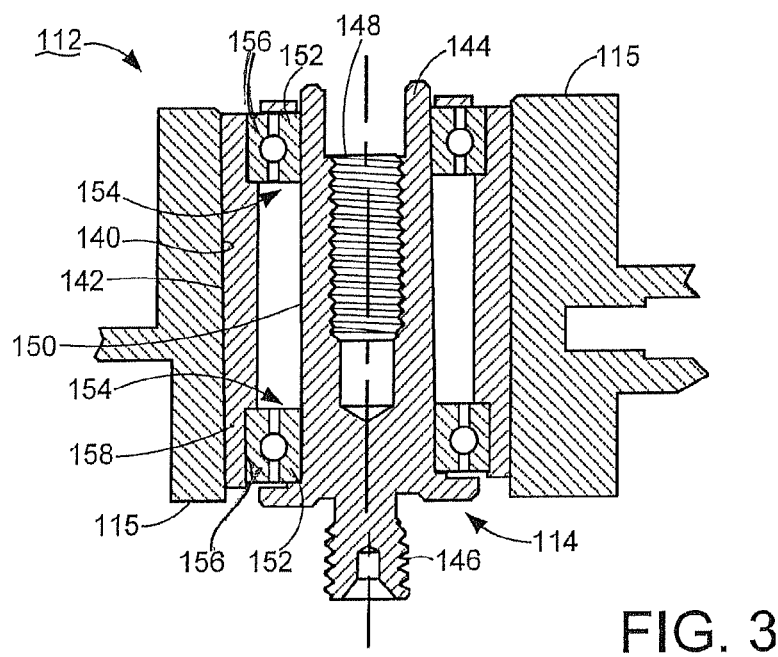
FIG. 3 is a cross sectional view of the cartridge bearing of FIG. 2.

FIG. 3 depicts a cross sectional view of the eblock 115 operably mounted to the cartridge bearing 114. In these illustrative embodiments the cartridge bearing 114 has a shaft 144 defining an externally threaded proximal end 146 for stationary attachment to the base 102 (FIG. 1), and an internally threaded distal end 148 for stationary attachment to the cover 104 (FIG. 1). The stationary shaft 144 also defines an internal mount 150 that is sized to matingly engage inner races 152 of each of two bearings 154 so that the inner races 152 are operably stationary too. Outer races 156 thereby operably rotate relative to the stationary shaft 144, with a hub 158 affixed to the outer races 156 in rotation together. As discussed, the external mount 142 (see also FIG. 2) is sized to matingly engage the bore 140 in the eblock 115 so that they are operably affixed together in rotation. In this manner, the eblock 115 is pivotable around the stationary shaft 144.

Figure 4:
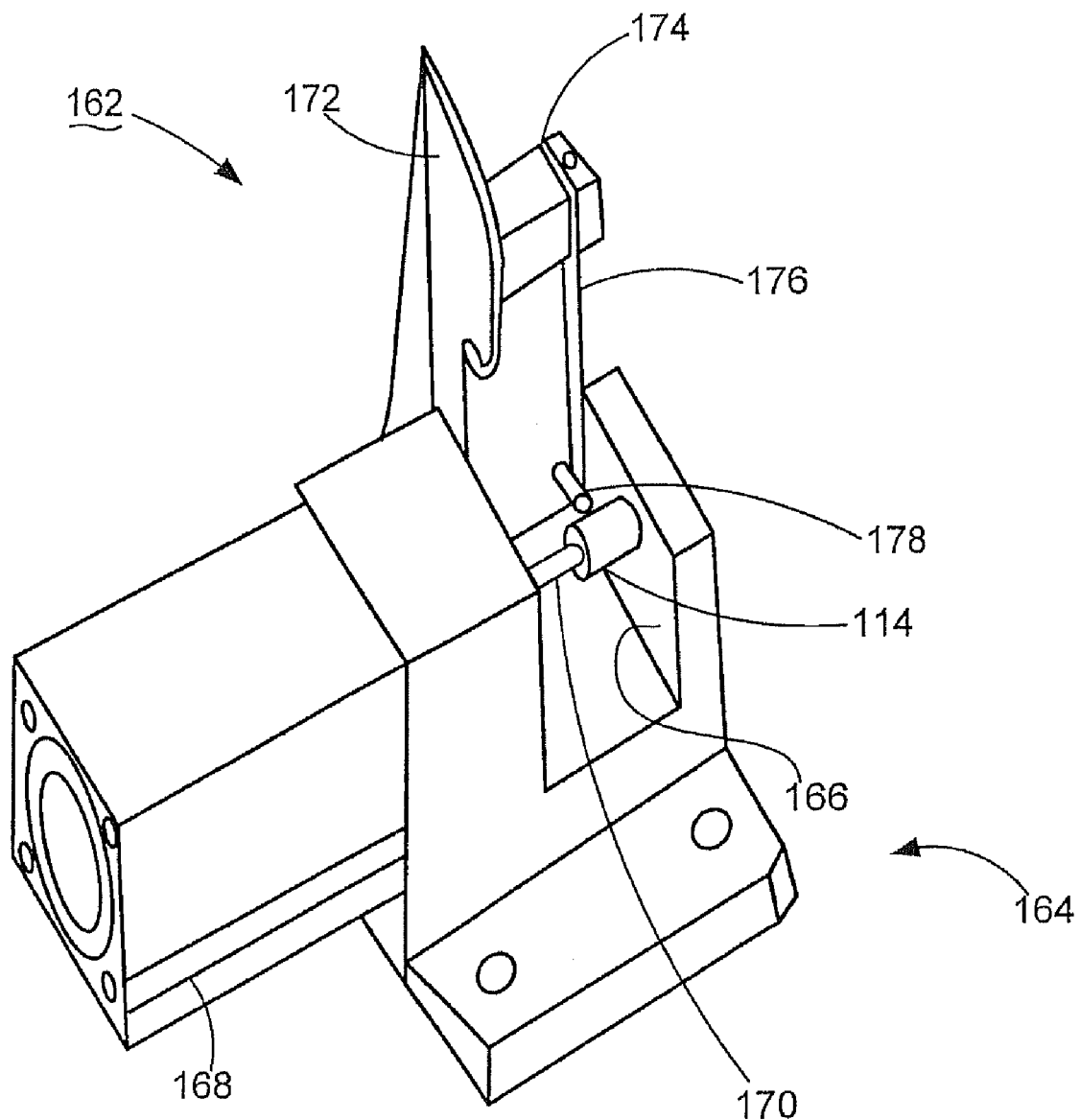
FIG. 4 is an isometric view of a bearing tester that is constructed in accordance with embodiments of the present invention.

FIG. 4 is an isometric view of a bearing tester 162 that is constructed in accordance with the claimed embodiments. A base 164 defines an upstanding surface 166 against which a bearing 114 under test is abuttingly fixtured. The base 164 supports a cylinder 168, such as a fluid-cylinder, that has an extensible shaft 170 to compressingly engage the bearing 114 against the surface 166. Alternatively, the cylinder 168 might be electrically or magnetically operated.

A stanchion 172 extends upwardly from the base 164 with a pivot 174 at an upper end thereof supporting a pendulum 176 that pivots in the path of a fixtured bearing 114. The pendulum 176 includes an impact hammer 178 of a known mass and which has an integrated accelerometer for indicating the acceleration with which the impact hammer 178 impacts against the bearing 114 during testing.

Figure 5:
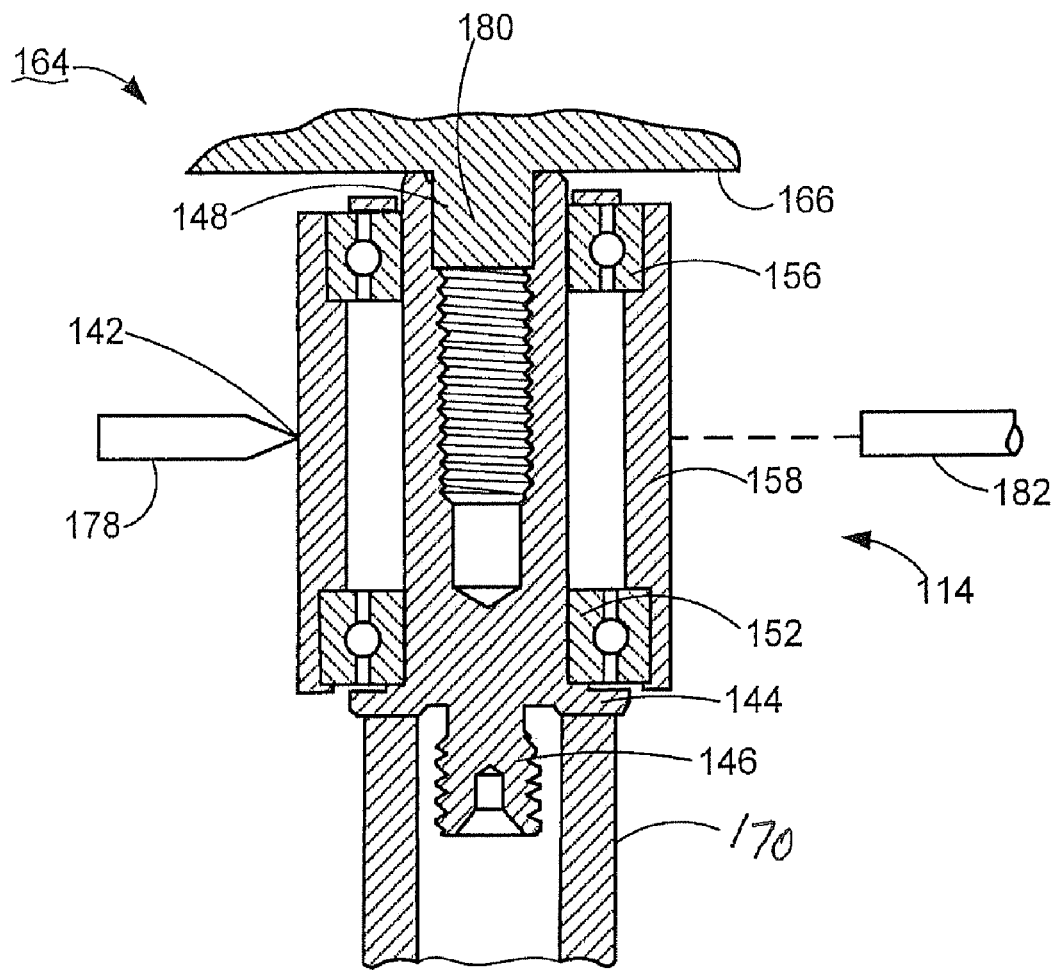
FIG. 5 is a partial cross sectional view of the bearing while being tested in the bearing tester of FIG. 4.

FIG. 5 is a top sectional view of the bearing 114 fixtured in the bearing tester 164. As described, the bearing 114 is compressingly engaged between the extensible shaft 170 and the upstanding surface 166. The latter defines a protuberant feature 180 that is sized to matingly engage a counterbore portion of the internal thread feature at the distal end 148 in order to precisely locate a bearing 114 for testing. The extensible shaft 170 is annular in its cross section so as to clearingly disengage the external thread feature at the proximal end 146. Thus, the opposing fixture members, the protuberant feature 180 of the surface 166 and the extensible shaft 170, hold the shaft 144 and inner races 152 stationary with respect to rotational movement while leaving the hub 158 and outer races 156 unencumbered.

However, the depicted embodiments for the bearing 114 and the opposing fixture members are illustrative and not limiting of the claimed embodiments. In alternative equivalent embodiments different fixture members can be provided in conjunction with different bearing 114 constructions, such as one having opposing protuberant features for a bearing 114 with an internal thread feature at both ends thereof.

FIG. 5 also depicts the impact hammer 178 precisely at the moment that it impacts (or "pings") the external mount 142 of the hub 158. Because the mass and acceleration of the impact hammer 178 are known, the impact imparts a predetermined mechanical force that excites the hub 158. A non-contacting motion sensing measurement device 182 is positioned radially opposite the impact hammer 178 at the point of impact to observe the resonance response of the hub 158 to the excitation. The resonance response can be used to qualitatively characterize the bearing 112 in terms of its radial stiffness.

Figure 6:
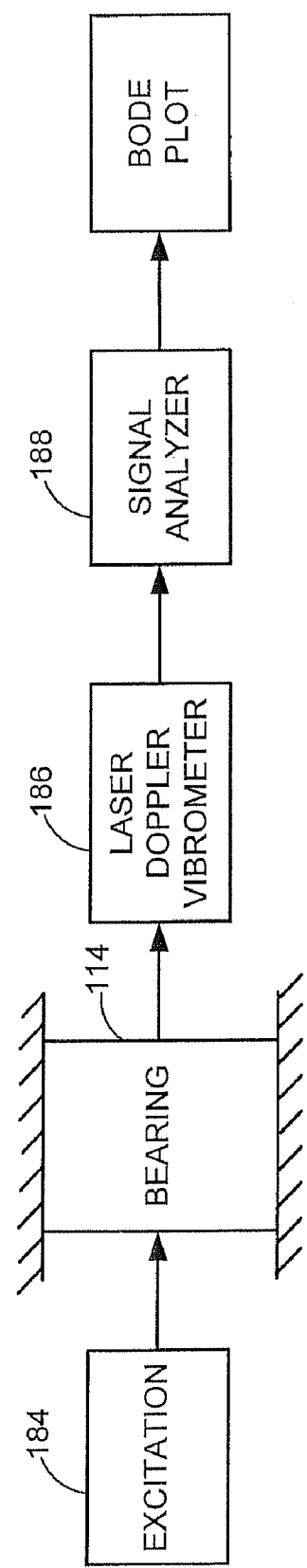
FIG. 6 is a functional block diagram of the bearing tester of FIG. 4.

FIG. 6 is a functional block diagram depicting illustrative embodiments of the bearing tester 162 of FIG. 4. As discussed above, the bearing 114 is fixtured so as to hold stationary the shaft 144 with respect to rotation, while leaving the hub 158 unencumbered. The impact hammer 178 delivers a mechanical excitation of a known predetermined force in block 184. The motion sensing measurement device, such as a laser Doppler vibrometer ("LDV"), detects the resonance response of the hub 158 to the mechanical excitation in block 186. The output signal from the LDV is analyzed in block 188 to provide results in a useful format. In these illustrative embodiments the signal analyzer performs a Fourier transformation on the LDV signature signal to produce a mechanical bode plot showing the resonance and phase relationship of the hub 158 in response to the excitation. Measured values can be compared to a predetermined threshold constructed across all frequencies of interest in order to qualitatively characterize a bearing 114 under test.

Generally, the embodiments described contemplate a bearing tester wherein a fixture operably holds an inner race of a bearing stationary with respect to rotational movement but leaves an external mount of the bearing unencumbered. The bearing tester also possesses a means for characterizing the bearing qualitatively in relation to an observed direct resonance response of the bearing to an excitation.

For purposes of this description and meaning of the appended claims, the phrase "means for characterizing" expressly means the structural aspects of the embodiments disclosed herein and the structural equivalents thereof. For example, without limitation, the disclosed testing of a bearing having the structural configuration depicted in FIG. 5 is illustrative of and not limiting of the present embodiments as claimed. For example, one may choose to test a bearing having externally threaded features or internally threaded features at both proximal and distal ends of the bearing, and incorporating appropriate fixture members to matingly engage such alternative embodiments is within the contemplated scope of the claimed embodiments. In another example, the fixture members can support the bearing longitudinally with respect to the impact hammer's path of travel in order to test a bearing's longitudinal stiffness.

However, the meaning of "means for characterizing" expressly does not include previously attempted solutions that first assemble the bearing into an actuator assembly or some subassembly, or where the mechanical excitation does not contactingly engage the bearing external mount such as in bode testing performed at the HAA level or in a shaker table excitation method.

It is to be understood that even though numerous characteristics and advantages of various embodiments of the present invention have been set forth in the foregoing description, together with details of the structure and function of various embodiments of the invention, this detailed description is illustrative only, and changes may be made in detail, especially in matters of structure and arrangements of parts within the principles of the present invention to the full extent indicated by the broad general meaning of the terms in which the appended claims are expressed. For example, the particular elements may vary in type or arrangement without departing from the spirit and scope of the present invention.

In addition, although the embodiments described herein are directed to a cartridge bearing, it will be appreciated by those skilled in the art that the claimed subject matter is not so limited and various other applications can utilize the present embodiments without departing from the spirit and scope of the claimed invention.

What is claimed is:

1. A method, comprising:
   holding an inner race of a bearing stationary with respect to rotational movement;
   retracting an impact hammer to noncontactingly disengage a hub that is fixed in rotation with an outer race of the bearing;
   after the retracting step, moving the impact hammer to contactingly engage the hub with a predetermined mechanical force; and
   characterizing the bearing qualitatively in relation to an observed resonance response of the hub to the moving step.

2. The method of claim 1 wherein the holding step comprises holding stationary a longitudinal shaft that is affixed to the inner race.

3. The method of claim 2 wherein the holding step comprises contactingly engaging the longitudinal shaft at two different portions thereof on opposing sides of the bearing.

4. The method of claim 3 wherein the holding step comprises compressingly engaging the longitudinal shaft between opposing fixture members.

5. The method of claim 4 wherein the holding step comprises at least one of the opposing fixture members comprising an extensible device selectively operable between an extended mode and a retracted mode.

6. The method of claim 5 wherein the holding step comprises the at least one of the opposing fixture members comprising a fluid pressurized extensible device.

7. The method of claim 1 wherein the moving step comprises contactingly engaging an external mount defined by the hub with the impact hammer.

8. The method of claim 1 wherein the moving step comprises the impact hammer being supported by a pendulum.

9. The method of claim 1 wherein the characterizing step comprises analyzing a signature vibration signal to create a bode plot of the resonance response.

10. An apparatus, comprising:
    a fixture that receiving engages a bearing to hold an inner race of the bearing stationary with respect to rotational movement;
    an impact hammer that is selectively positionable between a retracted position, where the impact hammer does not contact a hub of the bearing that is fixed in rotation with an outer race of the bearing, and an impact position, where the impact hammer contactingly engages the hub to impart a predetermined mechanical excitation to the bearing; and
    an analyzer that characterizes a resonance response of the hub to the mechanical excitation.

11. The apparatus of claim 10 wherein the fixture holds stationary a longitudinal shaft that is affixed to the inner race.

12. The apparatus of claim 11 wherein the fixture contactingly engages the longitudinal shaft at two different portions thereof on opposing sides of the bearing.

13. The apparatus of claim 12 wherein the fixture compressingly engages the longitudinal shaft between opposing fixture members.

14. The apparatus of claim 13 wherein at least one of the opposing fixture members comprises an extensible device selectively operable between an extended mode and a retracted mode.

15. The apparatus of claim 10 wherein the impact hammer contactingly engages an external mount defined by the hub.

16. The apparatus of claim 10 wherein the impact hammer is supported by a pendulum.

17. The apparatus of claim 10 wherein the analyzer comprises a laser Doppler vibrometer.

18. A bearing tester, comprising:
    a fixture that operably holds an inner race of a bearing stationary with respect to rotational movement but leaves an external mount of the bearing unencumbered; and
    means for qualitatively characterizing the bearing in relation to an observed direct resonance response of the bearing to an excitation.

* * * * *